Figure 1:
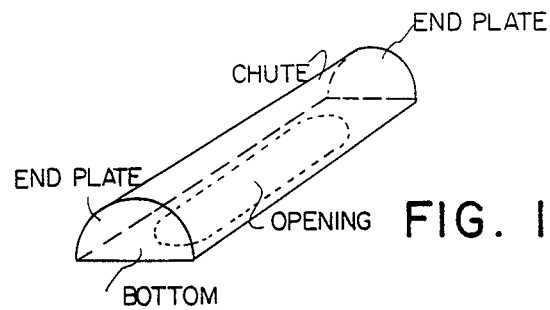

United States Patent [19]

Törmälä et al.

[11] Patent Number: 4,863,472
[45] Date of Patent: Sep. 5, 1989

[54] BONE GRAFT IMPLANT

[75] Inventors: Pertti Törmälä, Tampere; Pentti Rokkanen, Helsinki; Valle J. Oikarinen, Helsinki; Seppo Vainionpää, Helsinki; Pertti Helevirta, Tampere, all of Finland

[73] Assignee: Biocon Oy, Tampere, Finland

[21] Appl. No.: 192,741

[22] PCT Filed: Sep. 2, 1987

[86] PCT No.: PCT/FI87/00119
§ 371 Date: Jul. 5, 1988
§ 102(e) Date: Jul. 5, 1988

[87] PCT Pub. No.: WO88/01517
PCT Pub. Date: Mar. 10, 1988

[30] Foreign Application Priority Data

Sep. 5, 1986 [FI] Finland ................................ 863573

[51] Int. Cl.$^4$ ............................ A61F 2/28; A61C 8/00
[52] U.S. Cl. .................................. 623/16; 433/201.1; 623/66
[58] Field of Search .............. 623/16, 66, 12, 11; 435/201.1, 202.1, 212; 424/95; 106/35

[56] References Cited

U.S. PATENT DOCUMENTS 4,657,548 4/1987 Nichols ................................. 623/10
4,755,184 7/1988 Silveeberg ........................ 623/66 X Primary Examiner—Alan W. Cannon
Attorney, Agent, or Firm—Pollock, Vande Sande & Priddy

[57] ABSTRACT

Supporting structure (1) for preventing the movements of powder material (2) which will be applied as bone graft (bone graft powder) which supporting structure (1) will be located to contact with bone tissue and which supporting structure (1) is manufactured of at least partially resorbable polymer, copolymer or polymer mixture and is of its form chutelike, box-like, a flat tube or bag and contains such open porosity, which allows the surrounding tissues to grow through the supporting structure (1) but which prevents the migration of the bone graft powder (2) through the pores outside the supporting structure (1). The part of the supporting (1) which will be located against bone surface contains at least one orifice, whose size is bigger than the size of pores of the supporting (1) and bigger than the size of the bone graft powder (2) particles, which orifice makes possible the growth of the bone tissue into the inside of the supporting structure (1).

11 Claims, 2 Drawing Sheets

BONE GRAFT IMPLANT

It has been found that many ceramic materials have properties, which allow their use as bone graft materials. Ceramic materials (bioceramics), which are tissue compatible and/or which form chemical bonds with bone tissue and/or which promote the growth of bone tissue, are e.g. calciumphosphate: apatites like hydroxyapatite, HA, $Ca_{10}(PO_4)_6(OH)_2$ (R. E. Luedemann et al., Second World Congress on Biomaterials (SWCB), Washington, D.C., 1984, p. 224), trade names like Durapatite, Calcitite, Alveograf and Permagraft; fluoroapatites; tricalciumphosphates (TCP) (e.g. trade name Synthograft) and dicalciumphosphates (DCP); aluminiumoxide ceramics; bioglasses like $SiO_2$—$CaO$—$Na_2O$—$P_2O_5$, e.g. Bioglass 45S (structure: $SiO_2$ 45 wt-%, CaO 24,5% $Na_2O$ 24,5% and $P_2O_5$ 6%) (C. S. Kucheria et al., SWCB, Washington, D.C., 1984, p. 214) and glass ceramics with apatites, e.g. MgO 4,6 wt-%, CaO 44,9%, $SiO_2$ 34,2%, $P_2O_5$ 16,3% and CaF 0,5% (T. Kokubo et al., SWCB, Washington D.C., 1984, p. 351).

The application of the above ceramic materials as synthetic bone grafts has been studied by different means by using them for example both as porous and dense powder materials and as porous and dense macroscopical samples as bone grafts. Also ceramic powder-polymer composites have been studied in this means (e.g. W. Bonfield et al. SWCB, Washington D.C., 1984, p. 77). Hydroxyapatite is applied generally as bone graft material in powder form for alveolar ridge reconstruction by injecting the hydroxyapatite powder/water mixture (particle size typically 10–50 mesh) on the bony surface of alveolar ridge into a cavity which has been formed below the gingival tissue. The bone tissue grows into contact directly with hydroxyapatite particles, which are biostable and remain as part of the forming new bone.

The powder-like bone graft materials have, however, a disadvantage that they remain at their place only after the connective tissue and/or growing bone tissue binds them to their place. For example, in the case of hydroxyapatite powders applied for alveolar ridge augmentation this will take about one month. Before the powder particles have been bound to their place by means of tissue growth, the powder can move easily from the place, where it should be, when mechanical forces (e.g. biting) affect upon the soft tissues which surround the powder particles. This can lead to a deterioration of operation result and in the worst situation the desired bone graft effect is not achieved at all or it is achieved only partially.

The movements of the bone graft powder particles can be prevented by binding powder particles to each other by means of a polymeric material. Such materials have been described e.g. in G.B. Pat. No. 1 562 758, G.B. Pat. No. 1 593 288 and PCT-patent application 86/01113. The ceramic powder-polymer composites have a disadvantage that the presence of binding polymeric material prevents the direct contact of bioceramic powder particles and bone tissue to each other and therefore delays and prevents the growth of the bone tissue on the surface of composite material and inside of it, because the bone tissue does not have such an affinity to grow on the surface of biostable or resorbable organic polymers as it has to grow on the surface of bioceramics or into their internal open porosity. As a consequence the growth of new bone and the healing of tissue proceeds more slowly with bioceramics-polymer composites than with pure bioceramics (e.g. according to S. Ishida et al., ECB, Bologna, Italy, 1986, Abstracts, p. 86 the growth of new bone on the surface of 70% hydroxyapatite filler-triethyleneglycoledimethacrylate composite occured in studies done with rabbits 2–3 times more slowly than the growth of new bone on the surface of pure sintered hydroxyapatite.

The movements of the bone graft powder can be prevented also by closing the particles into a porous, flexible casing, whose pores are smaller than the particle size of the powder, but which pores are big enough to allow the growth of tissues through the pores. Such casing has been described in EP-patent application No. 82621. Porous, flexible casings, which have been manufactured e.g. of collagen or of resorbable (in tissue degradable) polymer, into which casings the bone graft powder is closed, separate, however, the bone graft particles and bone tissue surface from each other. When the direct contact of bone graft powder particles to the surface of the bone tissue is prevented, the growth of the bone tissue into the casing becomes more difficult and it may be even totally prevented. In such a case only connective tissue grows into the casing like Gongloff et al. found in animal experiments (R. K. Gongloff and C. K. Montgomery, J. Oral. Maxillofac. Surg., 43 (1985) 645; R. K. Gongloff, W. Whitlow and C. K. Montgomery, J. Oral. Maxillofac. Surg., 43 (1985) 570).

In this invention we have found unexpectedly that the movements of bone graft powder can be effectively prevented and on the other hand, the rapid growth of bone tissue into the bone graft powder can be obtained by putting on the bone surface during operation a supporting structure which is manufactured at least partially of resorbable polymer, copolymer or polymer blend and which is of its form chute-like, box-like, a flat tube or a bag. The bone graft powder is located inside and/or below this supporting structure and this supporting structure includes such open porosity, which allows the surrounding tissues to grow through the supporting structure but which prevents the migration of the bone graft powder through the pores outside the supporting structure. Especially that part of the supporting structure, which is located against bone surface contains at least one orifice, whose size is bigger than the size of pores of the supporting structure and bigger than the size of the bone graft powder particles. This orifice makes possible growth of the bone tissue into the inside of the supporting structure. Because the orifice of the supporting structure is bigger than the particles of the bone graft powder these get through the orifice into direct contact with the bone and therefore the bone tissue can rapidly grow inside of the supporting structure into the bone graft powder. FIG. 1 shows schematically a typical, chute-like supporting structure of the invention, in whose bottom is an orifice to help the ingrowth of bone tissue (the orifice has been drawn by a dot-line).

When the bone tissue grows inside of the supporting structure from the orifice and when connective tissue grows from sides and from above the supporting structure through its porosity inside the supporting structure it is fixed rapidly with the bone and soft tissues at the same time when the rapid ossification proceeds from the base of the supporting structure between the bone graft powder particles and also inside of them when it is a case of porous bone graft particles. As an additional support one can use resorbable fibers, or polymer to bind the bone graft particles together.

The supporting structure is resorbed and it is replaced later by connective- and/or bone tissue. In the same way is resorbed polymer or fibers which possibly are applied to bind powder particles together. As a consequence the bone tissue is augmented, remodelled or filled with new tissue, which comprises ceramic powder particles, bone tissue and connective tissue.

The orifice of the supporting structure can be closed by means of a thin ceramic plate with open porosity through which the bone tissue can grow. The orifice can be closed also by means of a rapidly resorbable film (e.g. by means of Poloxamer-polymeric film whose resorption time is below one day in vivo). Such a film dissolves rapidly after the operation and therefore allows formation of the direct contact between the bone graft powder and bone tissue surface for the growth of the bone tissue inside of the supporting structure at the same time when the resorbable supporting structure retains the form of the powder as desired.

This invention describes the above, at least partially resorbable supporting structures, their application to fill the defects in bone, to augment the bone tissue, like in the case of the augmentation of alveolar ridges, to change the form of bone tissue or in a corresponding meaning.

Resorbable polymers and copolymers are organic high molecular weight compounds, which are depolymerized in tissue conditions chemically and/or as a consequence of enzymatic activity. The materials which are depolymerized to monomer or oligomer level are metabolized by normal tissue reactions taking part e.g. to the energy producing reactions or to the synthesis of protein molecules. Accordingly, the surgical products and devices (implants) which are manufactured of resorbable polymers have an advantage that they are digested during a certain period of time without needing a separate removal operation, like implants which are manufactured of biostable materials (e.g. of metals) often need.

Table 1 shows typical nowadays known resorbable polymers which can be used in applications of this invention.

TABLE 1

| Resorbable polymers. |
|---|
| Polymer |
| Polyglycolide (PGA) |
| Copolymers of glycolide: |
| Glycolide/L-lactide copolymers (PGA/PLLA) |
| Glycolide/trimethylene carbonate copolymers (PGA/TMC) |
| Polylactides (PLA) |
| Stereocopolymers of PLA: |
| Poly-L-lactide (PLLA) |
| Poly-DL-lactide (PDLLA) |
| L-lactide/DL-lactide copolymers |
| Copolymers of PLA: |
| Lactide/tetramethylglycolide copol. |
| Lactide/trimethylene carbonate copol. |
| Lactide/δ-valerolactone copol. |
| Lactide/ε-caprolactone copol. |
| Polydepsipeptides |
| PLA/polyethylene oxide copolymers |
| Unsymmetrically 3,6-substituted poly-1,4-dioxane-2,5-diones |
| Poly-β-hydroxybutyrate (PHBA) |
| PHBA/β-hydroxyvalerate copolymers (PHBA/HVA) |
| Poly-β-hydroxypropionate (PHPA) |
| Poly-p-dioxanone (PDS) |
| Poly-δ-valerolactone |
| Poly-ε-caprolactone |
| Methylmethacrylate-N—vinyl pyrrolidone copolymers |

TABLE 1-continued

| Resorbable polymers. |
|---|
| Polymer |
| Polyesteramides |
| Polyesters of oxalic acid |
| Polydihydropyrans |
| Polyalkyl-2-cyanoacrylates |
| Polyurethanes (PU) |
| Polyvinylalcohol (PVA) |
| Polypeptides |
| Poly-β-malic acid (PMLA) |
| Poly-β-alkanoic acids |

Reference: P. Törmälä, S. Vainionpää and P. Rokkanen in IVA's Beijer Symposium "Biomaterials and Biocompatibility", Stockholm, Sweden, Aug. 25–26, 1987.

In addition to the above polymers there are many natural polymers and modified polymers, which are resorbable at least partially in tissue conditions and which therefore can be applied also according to the invention. Such polymers are for example collagen and its derivatives (Katgut, cross-linked collagen), chitine polymers, gelatine (cross-linked gelatin) and cellulose derivatives (for example trade name Surgicel).

The resorption rate of polymers in physiological conditions depends on many factors, like on the structure of the polymer, on the form of the resorbable sample and on its structure and on the biological environment. Therefore the resorption times of the above polymers can vary in different cases from about one week up to several years.

In the bone grafts of this invention can be applied especially well such resorbable polymers, copolymers or polymer mixtures or structures which are constructed of them, which retain at least part of their mechanical strength at least a couple of weeks and which are resorbed thereafter during several months. With special caution one can use also polymers which are resorbed more rapidly and on the other hand, the application of polymers which are resorbed more slowly does not cause as such disadvantage to the function of tissues.

The application of resorbable polymeric system as a part of bone graft implant which includes ceramic powder particles is specially advantageous in such cases, where the implants may be exposed to outer mechanical stresses, like for example happens in the case of alveolar ridge augmentation implants. The resorbable polymer system acts as a support and/or binds the ceramic particles together by preventing the movements of powder particles after operation when the connective and bone tissue begins to grow into the bone graft. In the later stages, when the ceramic powder has been ossified at least partially and it has been surrounded by the connective tissue, the resorbable polymer system dissolves as unnecessary and it is removed from the tissues by means of the normal metabolic ways.

According to this invention the polymeric system can be applied in relation to the ceramic powder phase either as inner and/or outer support in such a way that as a consequence of the supporting and/or binding effect of the polymeric system the outer shape of the bone graft implant remains essentially unchanged during the healing period.

If one applies the inner resorbable supporting structure of the powder phase it is obtained by binding the powder particles at least partially together by means of a resorbable polymer, which in this case acts as a gluephase between the particles and a composite material comprising powder particles and polymeric systems formed. Such a material can be manufactured for example by mixing ceramic powder with resorbable polymer and by melting or sintering the mixture to a solid sample, which in an advantageous form includes open porosity. Such a material can be manufactured also by wetting the ceramic powder with a solution of polymer, by forming of the wetted powder a sample and by evaporating the solvent. One can apply also other composite manufacturing methods which are known in the plastics technology. In the wetting polymer there can also be as reinforcements resorbable fibers, which increase considerably the strength properties of such a bone graft implant. The inner strong suporting structure can be manufactured also by binding the powder particles at least partially together by means of a resorbable, three-dimensional fiber structure, which can be net-like of its structure. In such a case the powder particles are bound to the meshes of the net. The fiber structure can be also sintered or melted partially possibly using pressure. In this case also the powder particles are sticked at least partially with the fiber structures.

It is advantageous that the internally bound or reinforced bone graft implant includes open porosity, (the pore size typically over 100 $\mu$m), into which living tissues can grow. When the connective and bone tissues grow around and inside the system comprising powder and supporting structure polymer the forces which bind the implant increase in the living tissue. Correspondingly, the strength of the resorbable supporting structure decreases and it is resorbed and replaced by the own tissues of the organism. At the end the resorbable supporting structure has been resorbed completely and the bone graft is changed to a part of the bone.

Figure 2A:
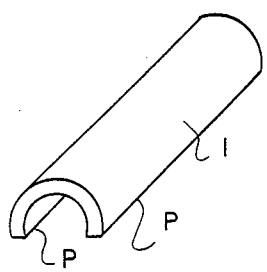
Figure 2B:
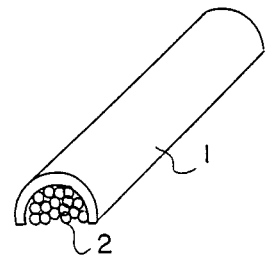
Figure 3:
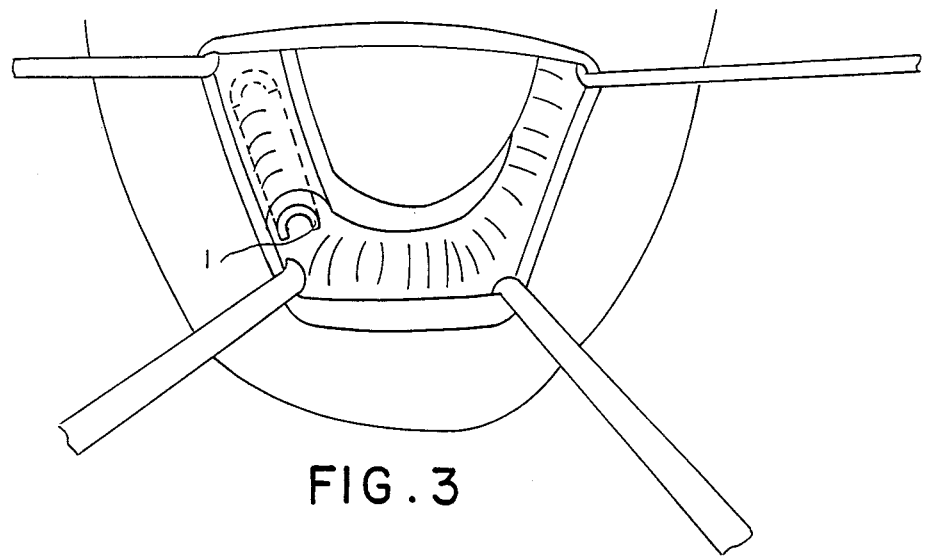

The resorbable supporting structure can be constructed of resorbable fibers or threads by weaving, knitting or some other corresponding method. The ceramic powder particles can be packed inside of such a supporting structure and the whole sample can be placed in an operation to a place in the bone tissue, where the bone graft is needed. The supporting structure can be manufactured also by the melt processing technique like by injection molding. The connective tissues which surround such a bone graft implant grow into the pores of the porous structure and also through the pores into the ceramic powder material and the bone tissue grows through the orifice of the supporting structure into the ceramic powder material as the same time, when the resorbable material begins to dissolve, when its supporting effect is no more needed. The external supporting structure of the bone graft implant which is manufactured of resorbable polymeric system can be also such a chute-like structure (1), as shown schematically in FIG. 2a, which is manufactured of resorbable polymer, copolymer or polymer mixture. Such a resorbable chute is especially advantageous as a part of a bone graft implant which is applied in alveolar ridge augmentation. In this case the bone graft implant comprises in addition to chute (1) of the ceramic powder (2) which is packed inside of the chute (FIG. 2b). The surgeon can apply the bone graft implant in an operation for example in such way that he makes on the surface of alveolar ridge below the gingival tissue an elongated subperiosteal tunnel, into which the resorbable chute (1) is pushed in such a way that the convex surface of the chute is directed to the gingival tissue and the end surfaces (p) of the sides of the chute are placed against the alveolar ridge. This situation is described schematically in FIG. 3 in the case a bone graft operation which is done to the right side of the mandible. Thereafter the the chute can be packed with ceramic bone graft powder and the wound of the gingival tissue can be closed. If necessary, one can place on the same alveolar ridge several chutes one after another.

Figure 2C:
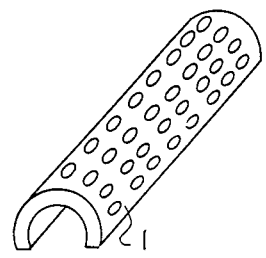
Figure 2D:
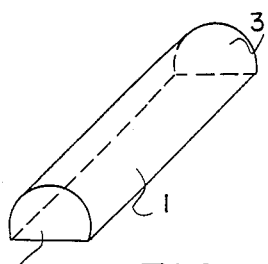
Figure 2E:
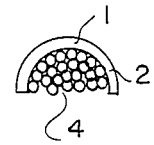
Figure 2F:
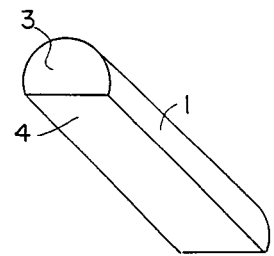

For a rapid healing it is advantageous that the resorbable chute contains open porosity or holes (e.g. FIG. 2c), because polosity and holes accelerate the growth of the tissue that surrounds the chute into it and into the ceramic powder. The ends of the chute can be open or closed by means of end plates (3), which comprise resorbable polymer, copolymer or polymer mixture like in FIG. 2d. The end plates of the chute (3) are made advantageously of the same material as the other parts of the chute. According to one advantageous embodiment (cross-section FIG. 2e) the ends (3) of the chute (1) are closed and the chute has been filled with ceramic bone graft powder (2) and the bottom of the chute has been closed by means of the thin, rapidly resorbable film (4), which can also be porous. This embodiment has been shown schematically in the cross-section FIG. 2e and in the perspective FIG. 2f. Such a bone graft implant can be pushed into the tunnel which has been done below the gingival tissue on the alveolar ridge in such a way that the thin, possibly pororus, rapidly resorbable film which closes the bottom of the chute is placed against the alveolar ridge. In this case the surgeon avoids the separate filling operation of the chute. When the bottom film is resorbed rapidly the bone tissue begins to grow from the alveolar ridge into the ceramic powder material which is inside of the chute, rapidly. The bottom film (4) can be manufactured also of a biostable polymer in such a way that it can be unfastened from the lower part of the chute (1) by drawing, after the chute has been placed into the tunnel on the alveolar ridge. Instead of a film the bottom of the chute can be closed also by means of a thin ceramic plate with open porosity (for example hydroxyapatite plate) through which the bone tissue can rapidly grow from the alveolar ridge.

Figure 4A:
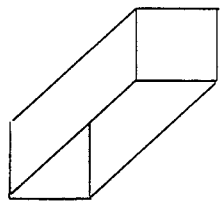
Figure 4B:
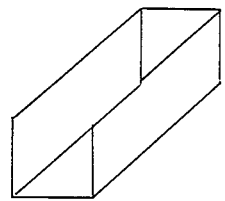
Figure 4C:
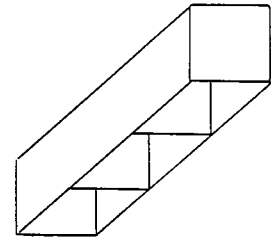

The external resorbable supporting structure of the bone graft implant can be also box-like (FIG. 4a), a box which is open of its end (FIG. 4b) or a box which contains honeycomb-like compartments (FIG. 4c). The bottom of the box or the bottoms of the compartments can be manufactured of a resorbable film or of a porous ceramic plate. Further the bottom of the box or the bottoms of its compartments can be manufactured of a biostable film or plate, which can be removed by drawing after the bone graft implant has been placed in operation into the living tissue.

Figure 5:
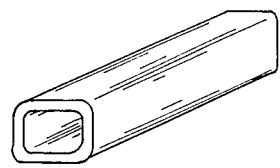

The outer resorbable supporting structure of the bone graft implant can be also of its form a flattened tube (FIG. 5) whose bottom part which is against the bone contains at least one orifice. Also the tube-like supporting structure can have the same structure and features as bag-like, chute-like and box-like supporting structures, when examining the porosity of the structure, holes, the use of end plates and the use of a special bottomplate or -film, by which also part of the periphery of the tube-like supporting structure can be replaced.

Also other analoguous supporting structures (casings) are self-evident solutions to the specialists.

An essential common feature of all the external resorbable supporting structures of the invention is that they prevent the unfavorable movements of the ceramic powder particles during the operation and during the first period of the healing, before the growth of the connective and bone tissue has locked the powder particles to their place.

According to an especially favorable embodiment the resorbable chute-like, box-like, tube-like or corresponding supporting structure of the resorbable bone graft implant contains also itself ceramic bone graft powder as disperged into the resorbable polymeric matrix. In this case the growth of tissues into the resorbable polymeric system happens especially advantageously, because the ceramic powder stimulates also in the region of the resorbable polymeric phase the growth of a new tissue.

According to an advantageous embodiment one can combine the internal support of resorbable polymeric system of powder phase with the external supporting structure which is constructed e.g. of resorbable fibers. Such a combination is especially good of its mechanical properties during the early period of the healing. In the bone graft of this invention one can apply ceramic powders or their mixtures which are described earlier in this application. Also the use of other synthetic ceramic powders or their mixtures and the use of powders which are obtained of bone materials (like xenografts, autografts or allografts) is self-evident for the specialists in this connection. In the method of this invention the unadvantageous movements of the bone graft powder particles, when the powder is placed into the tissue in bone graft meaning, are prevented by means of the supporting structure which is manufactured of resorbable polymer, copolymer or polymer mixture and possibly also by means of the tissues which surround the supporting structure at least partially.

The invention is illustrated by means of the following examples.

EXAMPLE 1

In a chute-like, heated, mold was manufactured resorbable supporting structures of bone graft implant (like those of FIG. 1) by pressing into the closed mold from a channel at the other end of the mould the melt of the resorbable polymer, which contained 40 wt-% hydroxyapatite powder (Durapatite 18–40 mesh, manufacturer Cook-Waite Laboratories, Inc.). The mold was cooled, opened and chute-like supporting structures of resorbable polymer and hydroxyapatite were obtained. The length of chutes was 40 mm, the wall thickness 1 mm and the curvature radius of the cross-section was 4 mm. The chutes were suitable to be used as external supporting structures of the bone graft implants for alveolar ridge augmentation. Table 2 shows the used resorbable polymers and the temperatures of polymer melts during the molding.

TABLE 2

The moulding temperatures in manufacturing chute-like supporting structures of bone graft implants.

| Polymer | The molding temperature |
| --- | --- |
| Poly-p-dioxanone | 115° C. |
| Poly-L-lactide | 185° C. |
| Poly-DL-lactide | 180° C. |
| Poly-β-hydroxybutyrate | 180° C. |
| Glycolide/lactide copolymer | 190° C. |
| Polyesteramide | 120° C. |
| Glycolide/trimethylene carbonate copolymer | 215° C. |
| Polyglycolide | 225° C. |
| Poly-β-hydroxypropionate | 120° C. |

TABLE 2-continued

The moulding temperatures in manufacturing chute-like supporting structures of bone graft implants.

| Polymer | The molding temperature |
| --- | --- |
| PHBA/PHVA copolymer | 150° C. |
| L-lactide/ε-caprolactone copolymer | 135° C. |

EXAMPLE 2

Chutes analogous with those of Example 1 were manufactured of polyglycolide (the wall thickness 0.4 mm). The chutes were made porous (open porosity) by forming in their convex surface and in their end plates a big amount of small holes with diameter of 0.3 mm, which holes penetrated the walls and the end plates of the chutes. These holes were formed by means of a hot needle. The chutes were filled with porous hydroxyapatite powder (particle size 0.6–0.8 mm, the manufacturer Interpore International) and the open bottom (the orifice) of the chutes was closed by melting on it a thin, rapidly resorbable film (the material; Poloxamer ®). These bone graft implants were placed into the teeth gap of mandibula of sheep on the alveolar ridge below the periosteum. Four sheep were treated. In histological studies which were done for two test animals after six weeks of operation it was found that hydroxyapatite powder had ossified partially beginning from the direction of the alveolar ridge. Additionally, the connective tissue had grown partially through the pores of the chute and the hydroxyapatite powder had retained well its macroscopical form due to the resorbable supporting chute. In histological studies done 12 weeks after the operation for two test animals it was found that the ossification had further increased inside of the hydroxyapatite powder and the macroscopical form of the powder had remained in good condition. In a comparison study into the teeth gaps of four sheep were placed corresponding chutes filled with hydroxyapatite powder. The open bottom (the orifice) of these chutes had been closed, however, by welding on it a 0.4 mm thick polyglycolide plate which contained a large amount of small pores (the pore size 0.3 mm) which pores penetrated the plate. In a histological study which was done six weeks after the operation for the test animals it was found that regardless of the open porosity of the polyglycolide plate the hydroxyapatite particles side of the chute were surrounded only by connective tissue.

We claim:

1. A supporting structure for preventing movement of powder material which is applied as bone graft which supporting structure will be located to contact bone tissue, wherein said structure contains bone grafts powder, said supporting structure comprising an at least partially resorbable polymer, copolymer or polymer mixture and having an open porosity for allowing surrounding connective tissues to grow through the supporting structure, but which prevents the migration of the bone graft powder through the pores wherein the part of the supporting structure which will be located against bone surface contains at least one orifice, whose size is bigger than the size of pores of the supporting structure, and bigger than the size of the bone graft powder particles, said orifice making possible the growth of the bone tissue into the inside of the supporting structure.

2. A supporting structure according to claim 1 wherein the bone graft powder comprises at least one of the materials consisting of: apatites, fluoroapatites, tricalcium phosphates, dicalcium-phosphates, aluminum oxide ceramics, bioglasses or glass ceramics containing apatite, and the resorbable supporting structure or binder polymer phase comprises at least one of the resorbable polymers consisting of: polyglycolides (PGA), polylactides (PLA), glycolide/lactide copolymers (PGA/PLA), glycolide/trimethylene carbonate copolymers (PGA/TMC), poly-$\beta$-hydroxybutyric acid (PHBA), poly-$\beta$-hydroxypropionic acid (PHPA), poly-$\beta$-hydroxyvaleric acid (PHVA), PHBA/PHVA copolymers, poly-p-dioxanone (PDS), poly-1,4-dioxanon-2,5-dione, polyesteramides (PEA), poly-$\epsilon$-caprolactones, poly-$\delta$-valerolactone, poly-carbonate, polyesters of oxalic acid, glycolic esters, and dihydropyranes.

3. A supporting structure according to claim 1, wherein the supporting structure is constructed of resorbable woven fibers.

4. A supporting structure according to claim 1, wherein the supporting structure has at least one end which is open.

5. A supporting structure according to claim 1, wherein the supporting structure has ends which have been closed by end plates, said end plates comprising a resorbable polymer, copolymer or polymer mixture and the end plates are of the same material as the other parts of the supporting structure.

6. A supporting structure according to claim 1, wherein said structure comprises a plurality of honeycomb-like compartments.

7. A supporting structure according to claim 1, wherein the orifice(s) of the supporting structure is (are) covered by a thin film or plate, comprising a rapidly resorbable polymer, copolymer or polymer mixture.

8. A supporting structure according to claim 1, wherein said structure contains ceramic bone graft powder dispersed in a resorbable polymer matrix.

9. A supporting structure according to claim 1 wherein said bone graft powder is admixed with a resorbable polymer as a binder.

10. A supporting structure according to claim 1 wherein said structure is constructed of resorbable knit fibers.

11. A supporting structure according to claim 1 wherein said structure is constructed of fibers which have been melted together.

* * * * *